United States Patent
Gruener

(10) Patent No.: US 8,089,263 B2
(45) Date of Patent: Jan. 3, 2012

(54) DEVICE FOR MEASURING THE STREAMING POTENTIAL OF FIBERS AND PARTICLES IN SUSPENSIONS

(75) Inventor: Giselher Gruener, Leipzig (DE)

(73) Assignees: Emtec Electronics GmbH, Leipzig (DE); AFG Analytic GmbH, Leipzig (DE)

( * ) Notice: Subject to any disclaimer, the term of this patent is extended or adjusted under 35 U.S.C. 154(b) by 702 days.

(21) Appl. No.: 12/096,709

(22) PCT Filed: Nov. 29, 2006

(86) PCT No.: PCT/EP2006/069050
§ 371 (c)(1), (2), (4) Date: Aug. 8, 2008

(87) PCT Pub. No.: WO2007/065825
PCT Pub. Date: Jun. 14, 2007

(65) Prior Publication Data
US 2008/0307862 A1     Dec. 18, 2008

(30) Foreign Application Priority Data

Dec. 10, 2005  (DE) .................. 20 2005 019 336 U
Jan. 12, 2006  (DE) .................. 20 2006 000 403 U
Feb. 22, 2006  (DE) ..................... 10 2006 008 569

(51) Int. Cl.
*G01N 15/06* (2006.01)
(52) U.S. Cl. .................. 324/71.1; 73/61.72
(58) Field of Classification Search .......... None
See application file for complete search history.

(56) References Cited

U.S. PATENT DOCUMENTS

| 3,368,392 A | | 2/1968 | Miller |
| 3,542,674 A | * | 11/1970 | Machlan ................ 210/709 |
| 4,687,986 A | | 8/1987 | Eriksson |
| 5,314,581 A | * | 5/1994 | Lin et al. ................ 162/263 |
| 5,510,702 A | * | 4/1996 | Eriksson ................. 324/71.1 |
| 6,176,974 B1 | * | 1/2001 | Hubbe ................... 162/158 |

FOREIGN PATENT DOCUMENTS

| DE | 3130529 A1 | 2/1983 |
| DE | 43 45 152 A1 | 3/1995 |
| DE | 20209563 U1 | 1/2003 |
| DE | 10200654 A1 | 7/2003 |
| EP | 0 462 703 B1 | 12/1991 |
| WO | 97/36173 A1 | 10/1997 |
| WO | 2004/015410 A1 | 2/2004 |

OTHER PUBLICATIONS

English Language Abstract for DE3130529.
English Language Abstract for DE20209563.
English Language Abstract for DE10200654.

* cited by examiner

*Primary Examiner* — Vinh Nguyen
(74) *Attorney, Agent, or Firm* — Norris McLaughlin & Marcus PA

(57) ABSTRACT

A device for measuring the streaming potential of fibers and particles in suspensions, in particular a device for determining the zeta-potential of the particles of aqueous suspensions containing fibers and particles, by measuring the streaming potential, and by subsequently computing the zeta-potential with an empirical formula. A periodic pressure curve is generated by arranging in the device for measuring the streaming potential at least two vacuum vessels, with each vessel having a different constant reduced pressure. The vacuum vessels are permanently set to a different vacuum and alternatingly connected via a valve to the measurement cell with the fiber plug. The required reduced pressure in the two vacuum vessels is maintained by using at least one small, low-capacity vacuum pump and a valve controller.

10 Claims, 2 Drawing Sheets

DEVICE FOR MEASURING THE STREAMING POTENTIAL OF FIBERS AND PARTICLES IN SUSPENSIONS

This application is a 371 application of PCT/EP2006/069050 filed Nov. 29, 2006, which claims priority to the German application DE 20 2005 019 336.4 filed Dec. 10, 2005, German application 20 2006 000 403.3 filed Jan. 12, 2006 and to German application 10 2006 008 569.8 filed Feb. 22, 2006.

The invention relates to a device for measuring the streaming potential of fibers and particles in suspensions, in particular a device for determining the zeta-potential of the particles of aqueous suspensions containing fibers and particles by measuring the streaming potential, and by subsequently computing the zeta-potential with an empirical formula.

BACKGROUND OF THE INVENTION

The characterization of surfaces and interfaces and of interactions taking place at those surfaces and interfaces is important for answering many questions arising in chemical, biotechnical and medical processes. In particular, for evaluating aqueous suspensions containing solids, emulsifying agents, fibers and other particles. The characterization of surfaces and interfaces and the interactions taking place at those places is of great importance in paper manufacturing. Electric effects at solid-liquid phase boundaries, the electric double layers and the related zeta-potential of the solid are characteristic for the respective material and its actual environment. The electric potential of the solid surface affects the absorption and adhesion of materials from the corresponding environment. The magnitude and the mathematical sign of the surface charge can be determined by measuring the so-called zeta-potential which describes the galvanic voltage at the diffuse electrochemical double-layer at the phase boundary between the surface of a solid and a fluid.

The zeta-potential of fibers in a fiber suspension is an important parameter in the paper industry for guaranteeing an optimal process flow. The same applies for textile fibers in the textile industry and for many types of particles in industrial processes. Several methods exist for determining this potential, for example:

Measurement of the drift velocity of the particles in the suspension in an electric field, from which the zeta-potential is computed, Measurement of the streaming potential of fibers or particles in the suspension, computation of the zeta-potential from the measured streaming potential by using an empirical formula.

EP 0 462 703 B1 describes a device for measuring an electric property, of a fiber dispersion. This device for measuring a pressure-dependent characteristic of a dispersion of solid material in a fluid consists of a means for transporting at least part of the fluid from a first chamber through a sieve into a second chamber for forming on the sieve a cushion of solid material and means for measuring the characteristic. This device has a pressure control device with at least one differential pressure controller, wherein the differential pressure controller is arranged such that a pressure signal commensurate with a predetermined pressure value is to be defined, and has additional means for withdrawing air from a second chamber with a defined velocity.

DE 43 45 152 A1 describes a zeta-potential measurement cell. The zeta-potential measurement cell for determining the zeta-potential on exterior and/or swelling surfaces of materials, which are stable under streaming conditions, includes a body which is provided with at least two intersecting through bores enclosing an angle of 90°. In one of the through bores, a rotatable and displaceable die, which is sealed against the body, is inserted from each opening of the through bore until the spacing is equal to the measurement gap. The end faces of the dies in the body are flat and mutually parallel, with a measurement gap located in between. The other through bore is formed as an entrance and exit channel for an electrolytic fluid, with the entrance and exit channel each having a respective electrode. The surface of the entrance and exit channel and of the dies in the body prevent direct electric connection between the two electrodes.

WO 97/36173 A1 describes a device for determining the charge density of dissolved, colloidal dissolved or undissolved, organic or inorganic materials in a sample fluid by titration, with a measurement container having at least two electrodes for receiving the sample fluid, with a piston which can be moved in the sample fluid with a motor about an operating position arranged in the measurement container, characterized in that stripper means for mechanically cleaning the piston and the vessel are provided.

A device for electro-kinetic analysis with a minimal fluid volume is described in DE 202 09 563 U1. The device is characterized in that an oscillating fluid stream is generated which can operate with small sample and fluid volumes, wherein in fibrous, powdered or granulated sample material the ratio of fluid volume to packed volume of the solid sample must not be greater than 10:1, and for planar samples the ratio of fluid volume to solid surface must not be greater than 0.5 $cm^3/cm^2$.

Other devices for measuring the streaming potential of fiber- and/or particle-containing aqueous suspensions operating according to various functional principles are known. In these devices, a fiber stopper or particle stopper is produced, for example, in a measurement cell which is open at the bottom and includes a suction tube, and which is closed on the top side with a sieve. This is attained by applying on a top sieve surface of the measurement cell a defined vacuum, thereby suctioning the suspension from, for example, a beaker and filling the measurement cell. This vacuum is generated with an external vacuum pump which is connected to a vessel connected with the measurement cell, wherein the vessel is located above the measurement cell and has a volume sufficient to receive the entire filtered matter/electrolyte of the suspension.

The suspension is suctioned via the preferably vertical suction tube located at the bottom side of the measurement cell, thereby forming the plug required for the measurement, because the sieve passes only water or the electrolyte, but practically no fibers or particles. The formed plug is simultaneously compressed by the reduced pressure in a manner required for an accurate measurement. The vacuum, which is permanently applied on the side of the sieve, ensures that the plug remains at its position. The filtered matter suctioned through the plug by the reduced pressure is collected in the vacuum vessel.

After the plug is formed, and even while the plug is formed, a periodical change in the reduced pressure produces a periodically change in the flow of the water of the suspension from the beaker through the plug. This flow produces a periodically change in the voltage caused by a deformation of charge clouds extending around the fibers or particles. The frequency of this periodic change is in the range of about 0.5 Hz to 10 Hz. The so-called streaming potential is measured with two electrodes located at the two ends of the measurement cell. The electrodes are made, for example, of stainless steel, platinum, silver or gold.

The zeta-potential is computed from the periodically changing streaming potential and the likewise periodically changing pressure difference relative to the ambient pressure, as measured with a pressure sensor, as well as from other variables. Advantageously, the periodic voltage change makes it possible to filter out DC offset voltages which can be generated, for example, by contamination and deposits on the electrodes. The periodically changing vacuum which produces the periodic flow through the plug, is produced with a powerful vacuum pump which is connected via two pressure reducing valves and two downstream valves and which is permanently active during the entire measurement. By alternatingly switching the valves, the vacuum in the vessel changes according to the reduced pressure defined by two pressure reducers. The vessel simultaneously receives the water or electrolyte which is suctioned from the beaker together with the suspension and flows through the plug and is filtered by the plug.

This process can be continued until the beaker with the suspension is empty. The plug is then removed from the vacuum vessel by applying ambient pressure to the upper portion of the measurement cell and as a result of the water flowing out due to gravity. The plug falls back into the beaker via the suction tube. Application of this functional principle is described, for example, in DE 102 00 654 A1.

Because the reduced pressure must periodically alternate in the vacuum vessel to produce the periodic fluid stream required for measuring the streaming potential, the relatively large volume of the vacuum vessel must be periodically switched from one value for the reduced pressure to the other value. In order to work at the required switching rate, a powerful and large vacuum pump is required, which is disadvantageous in particular, if suppliers of chemicals use the measurement device, for example, for different customers. The vacuum pump weighs approximately the same as the actual measurement device. The measurement device is therefore difficult to handle which complicates transport of the entire equipment.

In the aforedescribed state-of-the-art example, the temporal curve of the reduced pressure at the measurements cell and hence the streaming potential is periodically increasing and decreasing with a saw-tooth pattern, whereby the ratio of the increasing or decreasing section of the pressure curve and streaming potential curve in relation to the relatively constant section is very unfavorable due to the limited capacity of the vacuum pump and the required switching frequency of, e.g., 0.5 Hz. This means that there effectively exists no constant state, which complicates an exact computation of the zeta-potential, because the signals cannot be processed, for example, by filtering, due to their time dependence. However, exact measurement results can still be obtained by computing the zeta-potential including its mathematical sign from, for example, the streaming potential curve and the pressure curve through cross correlation.

In another method disclosed in WO 2004/015410 A1, the plug is produced in a container which is closed at one side with a sieve and is also closed with a sieve on the other side after the formation of the plug, either manually or by using a device. Thereafter, water or the electrolyte are pressed with periodically changing direction through the plug using one or two opposing motor-driven piston pumps, producing a periodic, in particular sinusoidal streaming potential, which is measured with electrodes. The zeta-potential can be computed from the streaming potential in conjunction with the measured difference pressure.

SUMMARY OF THE INVENTION

In this state-of-the-art embodiment, the plug to be measured must be produced manually, because the measurement cell is bounded on both sides by a sieve. This is necessary because in this case the flow direction of the filtered matter/the electrolyte changes periodically.

It is an object of the invention to propose an easily transportable and cost-effective device for measuring the streaming potential of fibers and particles in suspensions, in particular a device for measuring the zeta-potential of the particles in fiber- and/or particle-containing aqueous solutions by measuring the streaming potential and subsequently computing the zeta-potential with an empirical formula. The capacity and the size of the vacuum pump should be reduced to improve portability and reduce cost, wherein the vacuum should be constant within a half-period and should be instantaneously settable to the desired value.

The object is attained with the features of claim 1. Advantageous embodiments are recited in the dependent claims. The device of the invention for measuring the streaming potential of fibers and particles in suspension consists essentially of at least one vacuum pump, at least two vacuum vessels with pressure sensors, several valve assemblies, at least one pressure pump, at least one measurement cell with at least one sieve and a suction tube arranged in the measurement cell.

According to the invention, the disadvantages of the state-of-the-art are overcome by generating a periodic pressure curve, and by arranging in the device for measuring the streaming potential at least two vacuum vessels, each having a different constant reduced pressure. The vacuum vessels are permanently set to a corresponding different vacuum pressure and are alternatingly connected to the measurement cell with the plug via a valve, wherein the two vacuum vessels are permanently kept at the required reduced pressure by a small-capacity small vacuum pump with a valve controller. Alternatively, the two vacuum vessels can each be held at the required reduced pressure by a separate vacuum pump. The filtered matter streaming through the plug accumulates proportionally in the two vacuum vessels.

By switching from one vessel with a defined reduced pressure to the other vessel, the pressure at the plug formed in the measurement cell changes very rapidly. The curve of the streaming potential and the difference pressure at the measurement cell is then no longer saw-tooth-shaped, but is instead almost square. This significantly facilitates signal processing. The computation by cross-correlation can be eliminated.

In another embodiment, valves without an on/off characteristic are used; however, these valves can be controlled continuously and are therefore capable of generating a sinusoidal pressure curve at the measurement cell. Use of such valves also significantly facilitates signal processing. The computation by cross-correlation can be eliminated.

The streaming potential can be measured by averaging over the respective constant portion of the periodic signal and subsequently computing the difference. The computation for a sinusoidal potential curve can be performed, for example, by using the effective value or the peak value. Advantageously, the measurement frequency can be increased because the pressure at the measurement cell adapts quickly to the desired value, which also improves signal processing (variable offset voltages and low frequency interference) and also shortens the measurement process by decreasing the number of the measurement periods.

The portability of the device is improved significantly, because the small vacuum pump, which is now adequate, can be easily integrated in the device. In the aforedescribed alternative embodiment, a separate vacuum pump can also be employed for each vacuum vessel of the device.

The process flow of measuring the streaming potential of fibers and particles in suspension with the device of the invention takes is implemented as follows: one or several vacuum pumps integrated in the measurement device produce under the control of pressure sensors and valves a different, but constant, reduced pressure in two vacuum vessels which are connected to a measurement cell via valves. By switching one of the two vacuum vessels to the measurement cell, fiber suspension is suctioned into this measurement cell from a beaker through a suction tube. The upper section of the measurement cell is closed off by a sieve. This causes formation of a compact fiber plug in the measurement cell.

By alternatingly connecting a separate one of the two vacuum vessels, which are connected by valves to the upper portion of the measurement cell, a periodically changing reduced pressure is generated at the upper section of the measurement cell, which causes a periodic flow of water or electrolyte through the fiber plug. This produces a periodic streaming potential which is measured by two electrodes arranged at the upper and lower end of the measurement cell, respectively. From this streaming potential and the difference pressure as well as the conductivity of the electrolyte, the zeta-potential is then computed by a formula in an integrated microcomputer or an external computer.

After the measurement has been concluded, electrolyte for additional measurements can be withdrawn from one of the two vacuum vessels by applying an overpressure produced by a pressure pump.

For removing the fiber plug at the conclusion of the measurement and for emptying or cleaning the vacuum vessels, connecting hoses, valves and the measurement cell, an overpressure is produced in the vacuum vessels by the pressure pump. The overpressure presses the filtered matter or a previously introduced cleaning solution through the measurement device.

It is contemplated by the invention to design the device for measuring the streaming potential such as that vacuum is generated by several vacuum vessels for several suction tubes disposed in measurement cells, which significantly improves productivity. Moreover, according to the invention, pumps can be used which can operate both as a vacuum pump and a pressure pump. The weight of the device of the invention can then again be reduced for certain applications.

It is also feasible with the invention to design the device so as to be useful also for measuring the pH value. To this end, a sensor for measuring the pH value is arranged either in the lower region of the measurement cell or on the speaker containing the fiber suspension. The sensor for measuring pH value can also be placed at other locations with access to the fiber suspension or the filtered matter. The measurement results are acquired and processed by a microcomputer, and digitally displayed.

To enable other applications of the device, a metering device can optionally be integrated in the device of the invention in conjunction with a stirrer, for example a magnetic stirrer. Additives can be added to the fiber suspension with this metering device. These are additives which are added in an actual paper manufacturing process in addition to the fiber suspension to give the produced paper the desired consistency, structure and chemical composition. The metering device in conjunction with the stirrer is arranged on or immediately adjacent to the measurement cell, so that the added additives are introduced directly into the beaker. The metering device with the stirrer could also be flexibly affixed on the beaker.

The invention will now be described in more detail with reference to the exemplary embodiment illustrated in the drawing. The features depicted in the drawing and disclosed in the description can be used in other embodiments of the invention either separately or in any possible combination.

DETAILED DESCRIPTION OF THE INVENTION

Figure 1:
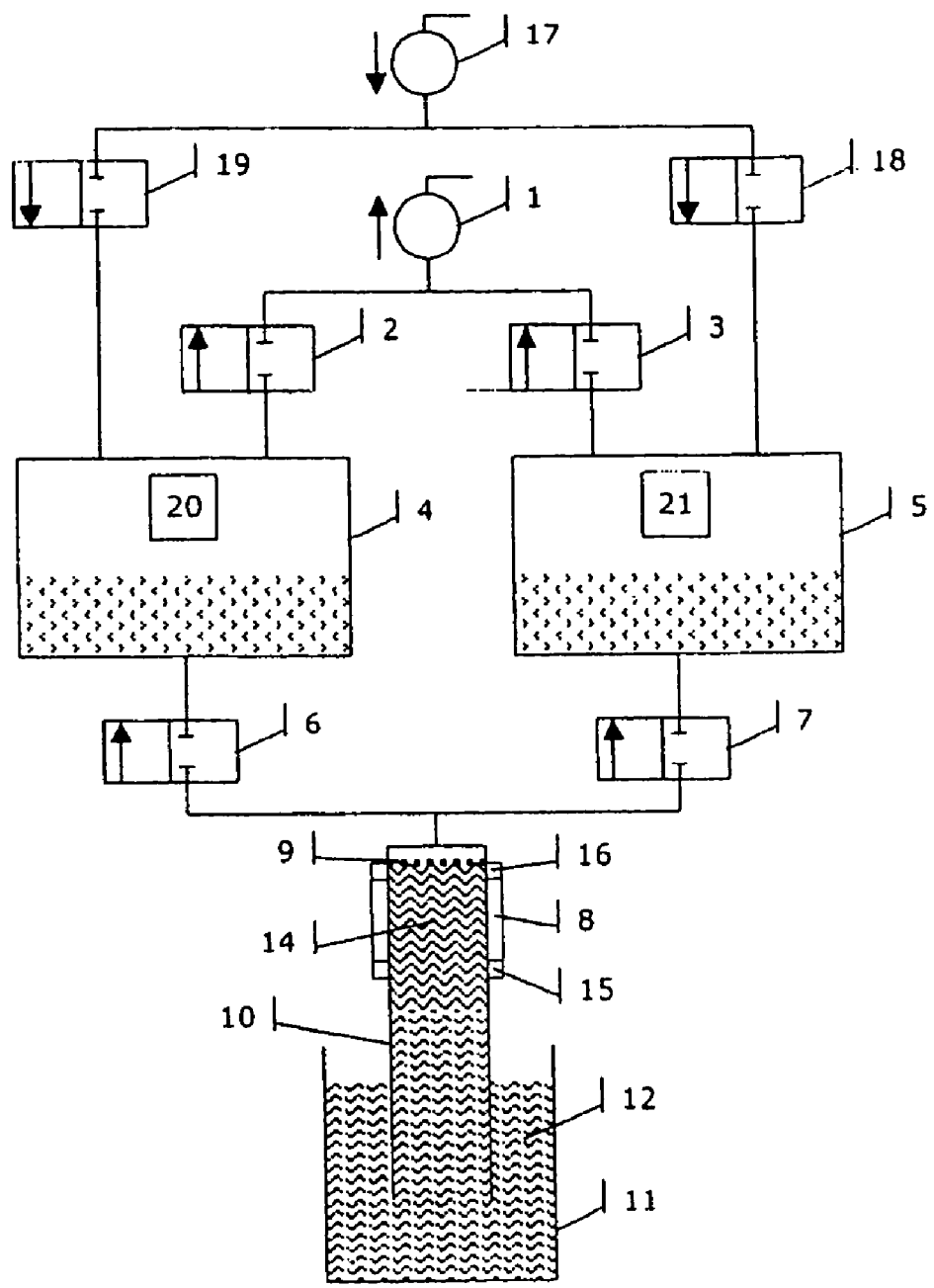
FIG. 1 a schematic diagram of a device with a single vacuum pump for measuring the streaming potential of fibers and particles in suspensions, and FIG. 2 a schematic diagram of a device with two vacuum pumps for measuring the streaming potential of fibers and particles in suspensions.
Figure 1:
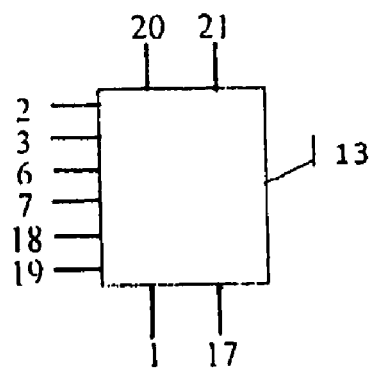

The device of the invention for measuring the streaming potential of fibers and particles in suspensions will now be described in more detail with reference to FIG. 1. The device consists essentially of a vacuum pump 1, two vacuum vessels 4; 5 with pressure sensors 20; 21, several valve assemblies, a pressure pump 17, a measurement cell 8 with a sieve 9, and a suction tube 10 arranged in the measurement cell 8.

The vacuum pump is connected via the valves 2 and 3 to two vacuum vessels 4 and 5, wherein a constant vacuum is produced in each of the vacuum vessels 4 and 5 under the control of the pressure sensors 20 and 21 and the valves 2 and 3. These vacuum vessels 4 and 5 are in turn connected via the valves 6 and 7 to the measurement cell 8, wherein the top side of the measurement cell 8 is closed off by a sieve 9 and has the suction tube 10 which extends into the beaker 11 containing the suspension 12 to be measured. All valves are controlled by a microcomputer 13 so that at the fiber plug 14, which is initially formed by permanent suction of suspension, a periodic streaming potential can be measured with two electrodes 15 and 16 made, for example, of stainless steel. A zeta-potential is computed from the streaming potential in conjunction with other measured parameters, e.g., a curve of the difference pressure or of the conductivity of the electrolyte.

The plug 14 is removed from the measurement cell 8 using a small pressure pump 17, which is connected to the two vacuum vessels 4 and 5 via two valves 18 and 19. The pressure pump 17 produces a slight overpressure which removes the filtered matter from the two vacuum vessels 4 and 5 and hence also pushes the plug 14 out of the measurement cell 8. The pressure pump 17 can also be used to withdraw filtered matter from one of the vacuum vessels 4 or 5 to perform additional measurements with the other measurement devices.

The measurement with the device of the invention for measuring the streaming potential of fibers and particles in suspensions 12 is made possible by the vacuum pump 1 which is integrated in the measurement device, in that the vacuum pump 1 produces a different constant reduced pressure in the vacuum vessels 4; 5, which are connected to a measurement cell 8 via the valves 6; 7, under the control of pressure sensors 20; 21 and valves 2; 3. By connecting one of the two vacuum vessels 4; 5 to the measurement cell 8, fiber suspension 12 is suctioned into the measurement cell 8 from a beaker 11 via a suction tube 10. The upper section of the measurement cell 8 is closed off by a sieve 9. This causes the formation of a compacted fiber plug 14 in the measurements cell 8.

By alternatingly connecting a respective one of the two vacuum vessels 4; 5, which are connected with the upper section of the measurement cell 8 via valves 6; 7, a periodically changing reduced pressure is produced at the upper section of the measurement cell 8, which causes a periodic flow of water and/or electrolyte through the fiber plug 14. This flow produces a defined streaming potential which is measured by two electrodes 15; 16 arranged on the upper and lower end of the measurement cell, respectively. From this streaming potential and the difference pressure as well as the conductivity of the electrolyte, the zeta-potential is computed with a formula in an integrated microcomputer 13.

After the measurement is concluded, an overpressure is produced in the vacuum vessels 4; 5 by the pressure pump for removing the fiber plug 14 and for emptying and/or cleaning the vacuum vessels 4; 5, the connecting hoses, valve assemblies and the measurement cell 8. The overpressure presses the filtered matter or a previously introduced cleaning solution through the measurement arrangement. After termination of the measurement, electrolyte can be withdrawn from one of the two vacuum vessels 4; 5 for carrying out additional measurements by applying an overpressure produced by the pressure pump 17.

Figure 2:
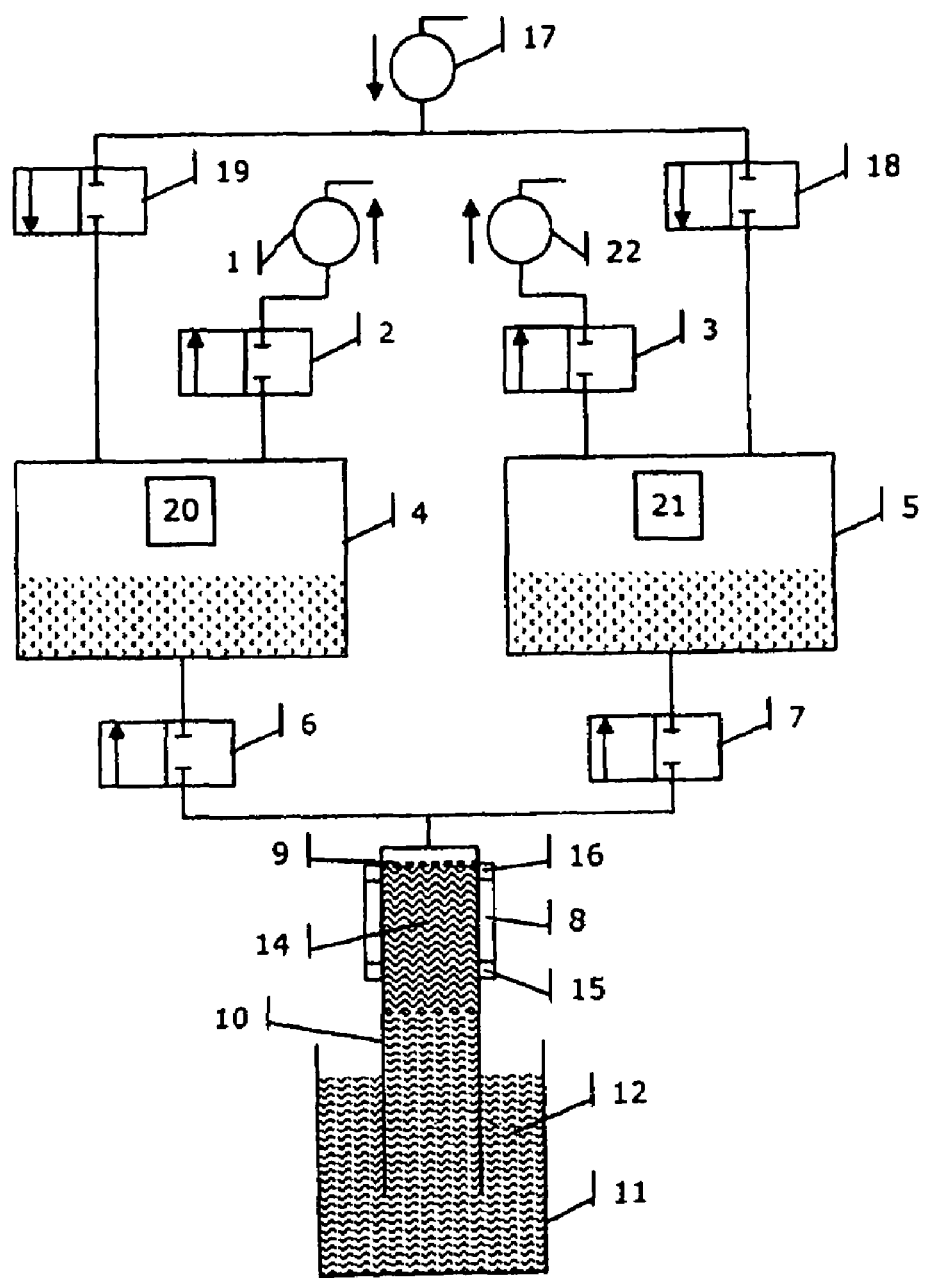
Figure 2:
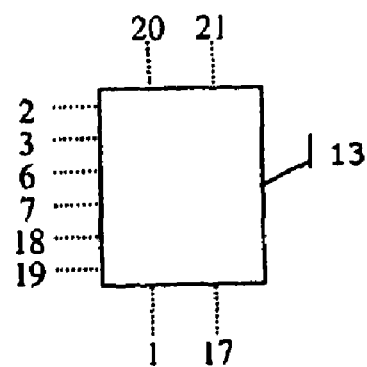

In this exemplary embodiment, the measurement device with at least two vacuum pumps 1; 22 according to FIG. 2 is described in more detail. The device of the invention for measuring the streaming potential of fibers and particles in a suspension according to this exemplary embodiment consists essentially of two vacuum pumps 1 and 22, two vacuum vessels 4; 5 with pressure sensors 20; 21, several valve assemblies, a pressure pump 17, a measurement cell 8 with a sieve 9, and a suction tube 10 arranged in the measurement cell 8.

The vacuum pumps 1; 22 are connected to two vacuum vessels 4 and 5 via the valves 2 and 3, wherein a constant vacuum is produced in each of the vessels under the control of pressure sensors 20 and 21 and the valves 2 and 3. These vacuum vessels 4 and 5 are in turn connected to the measurement cell 8 via the valves 6 and 7. The top side of the measurement cell 8 is closed off by a sieve 9 and includes the suction tube 10 which extends into the beaker 11 containing the suspension 12 to be measured. All valves are controlled by a microcomputer 13 so that a periodic streaming potential can be measured with two electrodes 15 and 16 made, for example, of stainless steel at the fiber plug 14, which is initially formed by permanent suction of suspension. A zeta-potential is computed from the streaming potential in conjunction with other measure parameters, e.g., a curve of the difference pressure or of the conductivity of the electrolyte.

The measurement with the device of the invention for measuring the streaming potential of fibers and particles in suspensions 12 according to this exemplary embodiment is made possible by the vacuum pumps 1 and 22 which are integrated in the measurement device, in that the vacuum pumps 1 and 22 produce a different, but constant, reduced pressure in the vacuum vessels 4; 5, which are connected to a measurement cell 8 via the valves 6; 7, under the control of pressure sensors 20; 21 and valves 2; 3. The subsequent process flow and removal of the plug 14 from the measurement cell 8 is performed in the same manner as described above with reference to Example 1.

What is claimed is:

1. Device for measuring the streaming potential of fibers and particles in suspensions, comprising a measurement cell (8) with a sieve and electrodes and a suction tube, wherein a vacuum pump (1) integrated in the device is connected with at least two vacuum vessels (4; 5) via valves (2; 3).

2. Device for measuring the streaming potential according to claim 1 wherein the vacuum vessels (4; 5) are connected to a pressure pump (17) via intermediate valves (18; 19).

3. Device according to claim 1, wherein each of the vacuum vessels (4; 5) is connected with a separately arranged pressure pump (17) via intermediate valves (18; 19).

4. Device according to claim 1, wherein each of the vacuum vessels (4; 5) is connected with the measurement cell (8) via intermediate valves (6; 7).

5. Device according to claim 1, wherein during a measurement process, a predetermined adjustable vacuum is present in the vacuum vessel (4) and a predetermined adjustable vacuum is likewise present in the vacuum vessel (5), with the vacuum in the vacuum vessel (5) being different from the vacuum in the vacuum vessel (4).

6. Device according to claim 1, wherein the vacuum vessels (4; 5) are connected to pressure sensors (20; 21).

7. Device according to claim 1, wherein a pumping device is provided which is operative to selectively generate a vacuum or a pressure.

8. Device according to claim 1, wherein valves (2; 3) are arranged between the vacuum pumps (1; 22) and the vacuum vessel (4; 5).

9. Device according to claim 1, wherein measurement results are acquired and processed by a microcomputer (13), and are digitally displayed.

10. Device for measuring the streaming potential of fibers and particles in suspensions, comprising a measurement cell (8) with a sieve and electrodes and a suction tube, wherein each of at least two vacuum pumps (1; 22) is separately connected with at least one corresponding vacuum vessel (4; 5) via two valves (2 and 3).

* * * * *

UNITED STATES PATENT AND TRADEMARK OFFICE
CERTIFICATE OF CORRECTION

PATENT NO.         : 8,089,263 B2
APPLICATION NO.    : 12/096709
DATED              : January 3, 2012
INVENTOR(S)        : Giselher Gruener Page 1 of 1

It is certified that error appears in the above-identified patent and that said Letters Patent is hereby corrected as shown below:

On the title page "(73) Assignees: Emtec Electronics GmbH" should read:

-- (73) Assignees: Emtec Electronic GmbH --

Signed and Sealed this
Twelfth Day of June, 2012

David J. Kappos
*Director of the United States Patent and Trademark Office*